United States Patent [19]

Wünsch et al.

[11] Patent Number: 5,041,533

[45] Date of Patent: Aug. 20, 1991

[54] HINGE PEPTIDE, A PROCESS FOR ITS MANUFACTURE, AND ITS USE FOR THE MANUFACTURE OF SYNTHETIC IMMUNOGENS

[75] Inventors: Erich Wünsch, Tutzing; Luis Moroder, Martinsried, both of Fed. Rep. of Germany

[73] Assignee: Max-Planck-Gesellschaft Zur Forderung der Wissenschaften E.V., Gottingen, Fed. Rep. of Germany

[21] Appl. No.: 175,383

[22] Filed: Mar. 30, 1988

[51] Int. Cl.$^5$ .......................... C07K 7/54; C07K 7/06
[52] U.S. Cl. ................... 530/317; 530/324; 530/326; 530/328; 514/11; 424/88
[58] Field of Search ............... 530/324, 326, 328, 317; 424/88; 514/11

[56] References Cited

U.S. PATENT DOCUMENTS 4,415,493 11/1983 Weigle et al. .
4,683,221 7/1987 Weigle et al. .

OTHER PUBLICATIONS

Kast (1973) Ann. Immunol. (Poznan) (Roland) 5 (3-4): 91-99.
Kabat (1980) Methods Enzymol. 70:3-49.
Kast R. E. (1973) Ann. Immunol. (Poznan) (Poland) 5/3-4=91-99, Abstract.

*Primary Examiner*—Jeffrey E. Russel
*Assistant Examiner*—Kay Kim
*Attorney, Agent, or Firm*—Venable, Baetjer, Howard & Civiletti

[57] ABSTRACT

The invention relates to a hinge peptide of the general formula I that may be utilized for the manufacture of synthetic immunogens. The invention also comprises a process for the manufacture of this hinge peptide and a process for the manufacture of synthetic immunogens, where the hinge peptide is employed as a carrier protein.

8 Claims, No Drawings

HINGE PEPTIDE, A PROCESS FOR ITS MANUFACTURE, AND ITS USE FOR THE MANUFACTURE OF SYNTHETIC IMMUNOGENS

BACKGROUND OF THE INVENTION

Research by Arnon, R. and Sela, M. (1969), *Proc. Nat. Acad. Sci. U.S.A.* 62, 163-170, and Arnon, R., Maron, E., Sela, M., and Afinsen, G. B. (1971), Proc. Nat. Acad. Sci. U.S.A. 68. 1450-1454 on the protein lysozyme using synthetic partial sequences has created the basis for the subsequent studies of a possible use of partial sequences from virus coat proteins or bacterial toxins which correspond to the antigenic regions of these pathogens to construct non-infectious substitute vaccines (Sela, M. (1974), *Bull. Inst. Pasteur* 72, 73-86; (4) Lerner, R. A. (1982) *Nature* (London) 199, 592; Sela, M. (1983) *Biopolymers* 415-424). Such synthetic vaccines were found to imitate the immunogenic potential of natural pathogens on the basis of the permanent immune response on the T and B cell plane and the full expression of the $T_h$ and B cells inducing determinants.

The general process of these experiments is currently based on the covalently linking via suitable reagents of synthetic peptide sequences of antigenic sequence domains of proteins to a carrier protein or to polymer compounds often with strongly immunogenic properties. The discovery of specific linking reagents has received increased attention Stevens, V. C. (1986), in *Synthetic Peptides as Antigens, CIBA Foundation Symposium* 119, Wiley, Chichester, pp. 200-225. In this connection, original research by the inventors has resulted in significant progress (Geiger, R., Moroder, L., and Wuensch, E. (1984) in *Peptides* 1984, (Ragnarsson, U., Ed.), Almquist and Wiksell Int., L Stockholm, pp. 451-456). Such peptide/protein conjugates have already been used for the immunization of experimental animals. The immune response can be further heightened by addition or incorporation of known immune adjuvants.

This research has led to the finding that (1) the dominant immune epitopes of viral coat proteins and bacterial toxins correspond to definite protein sequences in spatially fixed forms, and (2) the carriers of such epitope sequences not only contribute to a depot effect but also play a decisive role in the presentation of the epitope sequences for specific identification by the $T_h$ and B cells *Review: Synthetic Peptides as Antigens. CIBA Foundation Symposium* 119, Wiley, Chichester, 1986).

A synthetic vaccine against cholera and thermolabile *E. coli* toxin is described in DE-A1-34 30 894. The synthetic vaccine includes a product of the linking of a high molecular weight vehicle to a polypeptide corresponding to a part of the sequence of subunit B of the natural cholera toxin. The vehicle may be a suitable toxoid or a synthetic polymer of high molecular weight, such as an alanine-lysine polymer with a molecular weight of at least about 50,000.

The peptide chains of the immunoglobulins are known to be interconnected by way of a "hinge" region. The hinge region helps form the Y-shaped structure of the IgG molecule. The Y shape makes possible the flexibility of the IgG molecules required in antigen bonding.

SUMMARY OF THE INVENTION

The object of the invention is to create a versatile central molecule that may be used as a "hinge" region for linking peptide sequences comprising antigenic sequence regions.

The invention relates to a hinge peptide of the general formula I, described further below, that may be utilized for the manufacture of synthetic immunogens. The invention also comprises a process for the manufacture of this hinge peptide and a process for the manufacture of synthetic immunogens, where the hinge peptide is employed as a carrier protein.

DETAILED DESCRIPTION OF THE INVENTION

The requirements for an efficient immunogen as to a reproducible immune response and ultimately having neutralizing properties can unquestionably be successfully met only through the synthesis of a molecule having a definite structure with the incorporation of one or more epitopes of pathogens.

A central molecule of definite structure, provided with several different anchor points, is necessary as the carrier framework for the building of such synthetic miniproteins as immunogens. The inventors have now derived such a skeletal molecule from the primary structure of the immunoglobulins in the form of the hinge peptide. The central molecule—the hinge peptide of the present invention—is a double-stranded heterodetic cyclic cysteine peptide of formula I:

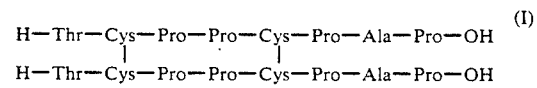

All the amino acids in this formula have the L-configuration.

The four anchor points, which can be extended by growing third-function amino acid residues as desired on the N and the C terminus, can be selectively protected. This permits controlled growing of several epitope sequences of the same or different primary structure in linear or cyclic form. In addition, a covalent linking of adjuvants of known nature, such as muramyl peptides or fatty acid derivatives of amino acids, is possible at all times.

It is possible to make certain changes in the central molecule of Formula I without impairing the properties of this peptide. Thus, for example, it is possible to replace the proline amino acid residue in one or more positions with a different amino acid residue, which guarantees the same spatial arrangement. The hinge peptide of the present invention may be designated by the general formula Ia:

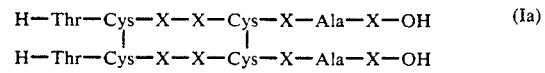

in which X is Pro or an amino acid equivalent to proline from the steric viewpoint. Other substitutions are also possible, as long as the general spatial arrangement is conserved.

In principle, the double chain of the hinge region may be in a parallel or anti-parallel arrangement. The parallel arrangement is more stable, and consequently is preferred. The parallel arrangement is illustrated in Formulas I and Ia.

The hinge peptide of the present invention has the advantage that it is relatively small and rigid. The resulting stability is also transferred to the immunogens constructed from the hinge peptide which, for example, has a favorable effect on enzyme stability. The hinge peptide of the invention possesses several functionalities which can be protected in whole or in part with customary protein protective groups such as BOC, FMOC (fluorenylmethoxycarbonyl), Nps (2-nitrophenylsulfenyl), tBu (=tert. butylester and ter. butylether), Acm (acetylaminomethyl), and trityl, by conventional methods.

In theory, it would be possible to derive the hinge peptide of the invention by separating it from natural immunoglobulins. However, this procedure is unpractical both because of the disproportionately high cost and the danger of introducing impurities into the final product. This danger would be similar to the danger present in the manufacture of vaccines form natural sources, which precisely is desired to be avoided through manufacture of synthetic vaccines.

Various methods are available for synthesis of the hinge peptide of the present invention, as shown in Scheme 1 or Scheme 2.

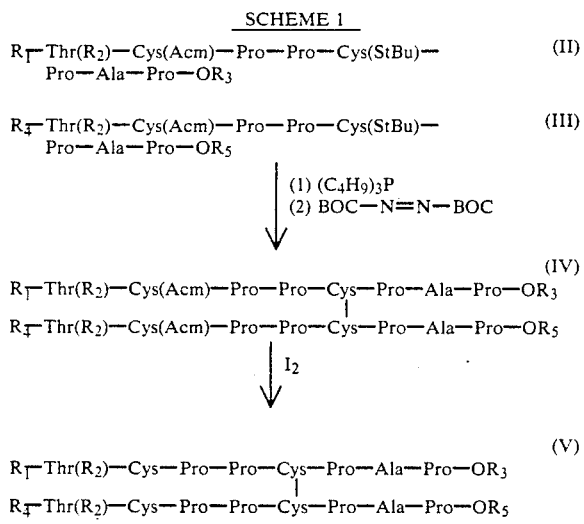

$R_1$, $R_2$, $R_3$, $R_4$ and $R_5$ are H or conventional protective agents such as BOC, FMOC or Nps for $R_1$ and $R_4$, and Bu for $R_2$, $R_3$ and $R_5$. Peptide derivatives II and III of the two chains of the hinge peptides are synthesized by well known methods for conventional peptide synthesis in solution, such as described in 10) Houben-Weyl *Methoden der Organischen Chemie,* Vol. 15 I/II (Wuensch, E., Ed.), Georg Thieme, Stuttgart, 1984. The tert.-butylthio residues of II and III are then reductively separated by means of phosphines, such as by the procedure of (11) Moroder, L., Gemeiner, M., Goehring, W., Jaeger, E., Thamm, P., and Wuensch, E. (1981), *Biopolymers* 20, 17–37. The cystine peptides are selectively cross-linked to form the monocystine peptide IV using azodicarbonic acid derivatives, such as in the procedure described by (12) Wuensch, E., Romani, S., Hoppe-Seyler's, *Z. Physiol. Chem.* 363 (1982), pp. 449–453. The second cysteine bridge is then selectively supplied by iodine oxidation of peptide derivative IV by suitable methods such as those described by (13) Kamber, B. and Rittel, W. (1968), *Helv. Chim. Acta* 51, pp. 2061–2064. Peptide derivatives of the general formula V are thereby obtained.

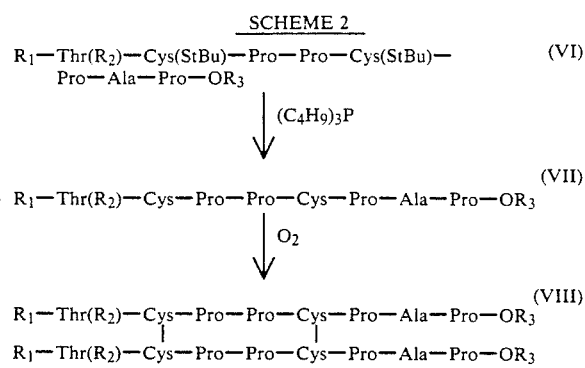

Alternatively, the octapeptide derivative VI is synthesized by a conventional peptide synthesis procedure. Separation of the two tert.-butylthio groups is again accomplished by reduction with phosphines ((11) Moroder, L., Gemeiner, M., Goehring, W., Jaeger, E., Thamm, P., and Wuensch, E. (1981), *Biopolymers* 20, pp. 17–37). The resulting bis-cysteine peptide derivative is transferred to the hinge peptide derivative VIII by air oxidation in concentrations of $10^{-3}$ to $10^{-4}M$. The parallel arrangement of the two chains is preferred to such an extent from the viewpoint of energy that exclusively the product of formula VIII is obtained. This has been proved by comparative studies of hinge peptide preparations obtained by Scheme 1 (controlled disulfide bridge formation) and Scheme 2.

The structures of the hinge peptides can be confirmed by a wide variety of analytical methods, such as determination of molecular weight by osometric methods, amino acid analysis following acid hydrolysis and enzyme decomposition, the racemate test, and high-resolution nuclear resonance spectroscopy. The uniformity of these products has been demonstrated by means of chromatographic analysis tests.

The hinge peptide of the invention can be used advantageously for the manufacture of synthetic immunogens. Hence the invention also comprises a process for the manufacture of synthetic immunogens. A hinge peptide of the invention is employed as a carrier protein and is covalently bonded by known methods to peptide sequences, preferably synthetic peptide sequences, comprising the antigenic sequence regions of proteins.

An example of synthesis of epitope conjugates is shown in Schemes 3 and 4, using the gastrin hinge peptide as a model.

SCHEME 3

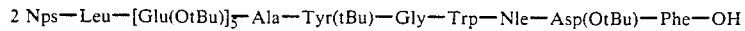

2 Nps—Leu—[Glu(OtBu)]₅—Ala—Tyr(tBu)—Gly—Trp—Nle—Asp(OtBu)—Phe—OH          (IX)

+

-continued
SCHEME 3

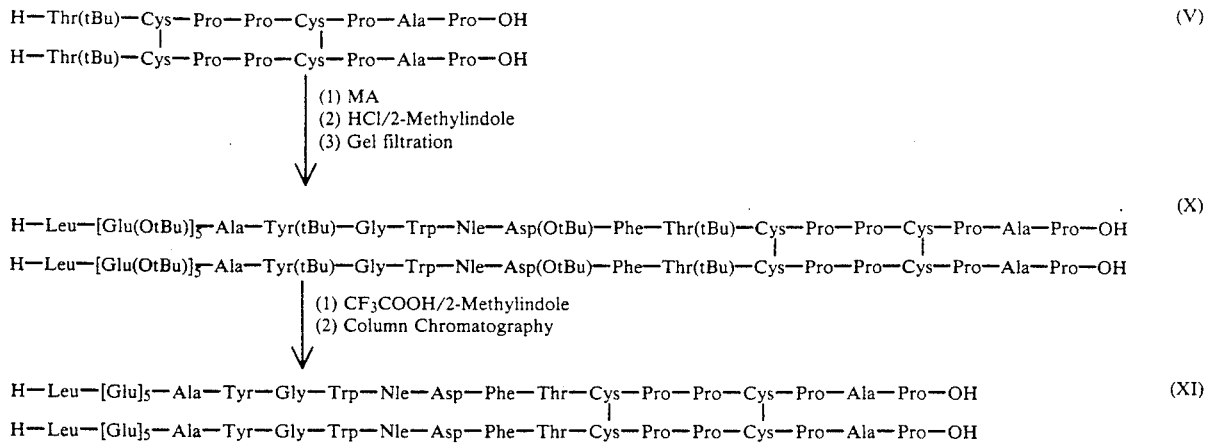

The Nα and side chain protected gastrin peptide of sequence 6–17 of the norleucine-15 analog of human-little-gastrin-IIX is prepared by conventional techniques. The gastrin peptide (IX) is covalently bonded by the mixed anhydride method to both N termini of hinge peptide derivative V, prepared as previously described, with optimum yield. Following protective group separation of X with HCl in the presence of 2-methylindole and trifluoroacetic acid/2-methylindole, the desired gastrin hinge peptide conjugate XI is obtained is a uniform product through gel filtration and partition chromatography with cellulose.

SCHEME 4

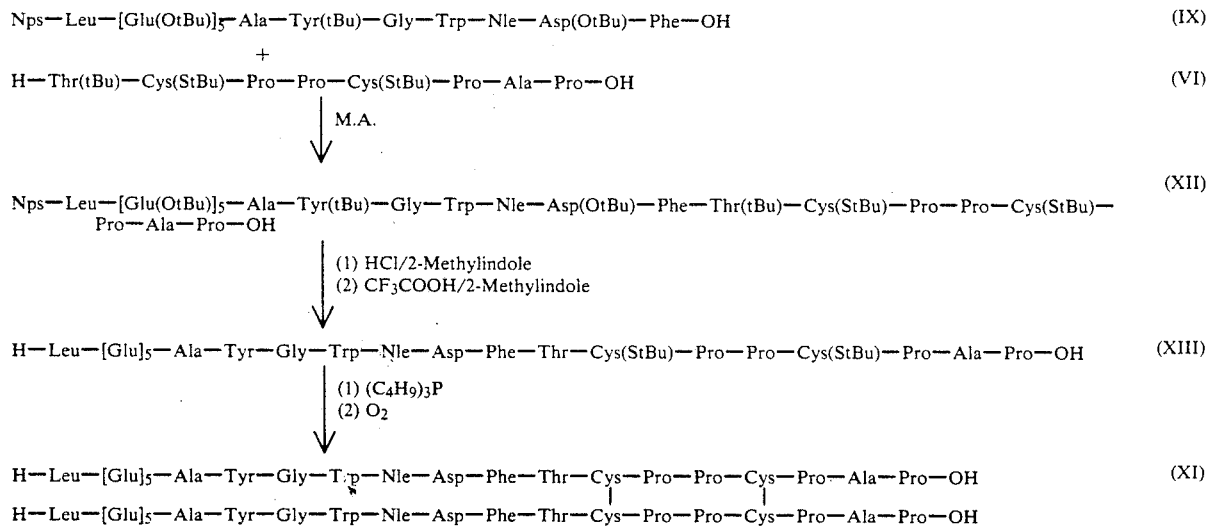

Alternatively, the suitably protected gastrin peptide IX is linked by the mixed anhydride method with the octapeptide VI to produce derivative XII. Following separation of the acid-labile protective groups in two stages and intermediate cleaning by column chromatography, the cysteine protective groups were then removed from the resulting peptide derivative XIII reductively by the phosphine process. The bis-cysteine peptide obtained was transferred to the gastrin hinge peptide conjugate XI by air oxidation as previously described with optimum yields. The gastrin hinge peptide conjugates obtained by Scheme 3 or 4 were found to be identical in all analytical tests conducted.

EXAMPLES

EXAMPLE 1a

Nos-Thr(tBu)-Cys(Acm)-Pro-Pro-Cys(StBu)-Pro-Ala-Pro-OH   (IIb)

This product was prepared by conventional peptide synthesis in accordance with Scheme 1 described above. Melting point 100–105° C.; $[\alpha]^\circ D = -205.3°$ C. or $[\alpha]^{20}546 = -244.9°$ C. (c=1, methanol); amino acid analysis: Thr 0.78 (1)* Pro 3.93 (4) Ala 1.00 (1) Cys 1.99 (2); racemate test: D-ala 0.4%; D-allo-Thr 1%; D-Pro 1%.

* Calculated values in parentheses.

Elementary analysis for $C_{50}H_{76}N_{10}O_{13}S_4 \cdot H_2O$ (1171.5):
Calculated: C, 51.26: H, 6.71: N, 11.96: S, 10.95
Found: C, 51.48: H, 6.72: N, 11.59: S, 10.76

EXAMPLE 1b

H-Thr(tBu)-Cys(Acm1-Pro-Pro-Cys-Pro-Ala-Pro-OH   (IIIb)

A yield of 93% was obtained through reduction of IIb with 5 equiv. tributylphosphine in 95% trifluoroethanol (3 h at room temperature) as described in Scheme I.

$[\alpha]^{20}D$ −18.2° C. or $[\alpha]^{20}546 = -217.3°$ C. (c=1, methanol).

Elementary analysis for $C_{40}H_{65}N_9O_{11}S_2$ (912.15):
Calculated: C, 52.67; H, 7.18; N, 13.82; S, 7.03
Found: C, 52.63; H, 7.20; N, 13.49; S, 7.09

EXAMPLE 1c

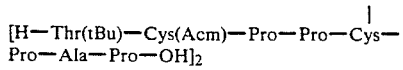
(IVb)

Oxidation of IIIb as in Scheme 1 with 0.5 equiv. azodicarbonic acid-di-tert.-butylester in dimethylformamide produced the title compound.

Yield 81%; melting point 180°–185° C. (decomposition); $[\alpha]^{20}D = -204.0°$ C. or $[\alpha]^{20}546 = 243.4°$ C. (c=1, 80% acetic acid).

Amino acid analysis: Thr 1.34 (2) Pro 7.92 (8) Ala 2.00 (2) Cys 4.02 (4) peptide content 92%.

EXAMPLE 1d

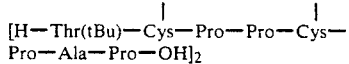
(Vb)

Dropwise addition of IVb in 80% acetic acid (c=2×10⁻³M) to iodine in 80% acetic acid (5 equiv., c=1× 10⁻²M) for a final peptide concentration 1×10⁻³M yielded the named compound.

Yield: 74%; melting point 215°–220° C. (decomposition); $[\alpha]^{20}D = -321.0°$ C. or $[\alpha]^{20}546 = -382.6°$ C. (c=80% acetic acid). Amino acid analysis: Thr 1.60 (2) Pro 7.83 (8) Ala 2.00 (2) Cys 4.00 (4); peptide content 98%. Racemate test: D-Ala 0.8%; D-allo-Thr 0.8%; D-Pro <1%. Osmometric molecular weight determination: actual: $M_r = 1,470$; theoretical: $M_r = 1,678.1$.

Elementary analysis for $C_{74}H_{116}N_{16}O_{20}S_4 \cdot 5H_2O$ (1,768.1):
Calculated: C, 50.27; H, 7.18; N, 11.67; S, 7.25
Found: C, 50.20; H, 7.08; N, 12.70; S, 7.02

EXAMPLE 1e

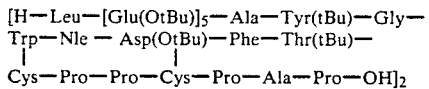
(Xb)

Derivative Vb (1 equiv.) was linked with the gastrin peptide (3 equiv.) Nps-Leu-[Glu(OtBu)]₅-Ala-Tyr(tBu)-Gly-Trp-Nle-Asp(OtBu)-Phe-OH (IX), which was prepared by conventional peptide synthesis, by the mixed anhydride method as described in Scheme 3. The Nps protective group was separated with HCl in N-methylpyrrolidone in the presence of 2-methyl indole to produce the title derivative. The derivative was purified by gel filtration with LH60 (N-methylpyrrolidone as solvent); yield 35%.

Amino acid analysis: Asp 2.14 (2) Thr 1.76 (2) Glu 9.40 (10) Pro 8.22 (8) Gly 2.12 (2) Ala 4.20 (4) Cys 4.22 (4) Leu 1.86 (2) Nle/Tyr 4.16 (4) Phe 2.18 (2); peptide content 85% ($M_r = 5,759.9$ as dihydrochloride).

EXAMPLE

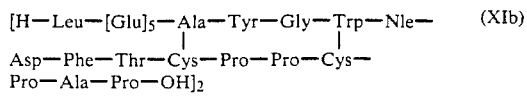
(XIb)

Compound Xb was treated with 99% trifluoroacetic acid/anisole (10:1) in the presence of 2-methylindole (50 equiv.). The named product was purified by gel filtration with Fractogel HW-40/S (eluent: 1M ammonium acetate/2-butanol/2-propanol, 100:16:1.5, ph 7.2) and by partition chromatography with cellulose (eluent: 0.05M ammonium acetate/2-butanol/1-butanol/2-propanol, 20:10:4.4, ph 5.5). Amino acid analysis of the HCl hydrolysate: Asp 2.09 (2) Thr 1.72 (2) Glu 9.59 (9) Pro 7.93 (8) Gly 2.14 (2) Ala 3.99 (4) Cys 4.24 (4) Leu 2.00 (2) Nle/Tyr 3.95 (4) Phe 2.03 (2) Trp 1.92 (2): peptide content 86.6% ($M_r = 4.78.4$). Following reduction with dithiothreitol and S-carboxymethylation with iodoacetic acid, XIb was digested with aminopeptidase M/prolidase for amino acid analysis. Amino acid analysis: Asp 2.06 (2) Thr 1.84 (2) Glu 9.96 (10) Pro** 6.60 (8) Gly 2.00 (2) Ala 3.94 (4) Nle/Tyr 3.82 (4) Phe 2.02 (2) Trp 1.80 (2) Leu and S-carboxymethyl-cysteine not determined (Leu because of TRIS buffer overlapping).

** Prolidase as well does not digest Pro-Pro sequences quantitatively.

Immunizations with Gastrin Hinge Peptide Conjugate

Freunds' adjuvant was added by a known process ((14) Turkelson, C. M., Dale, W. E., Reidelberger, R., and Solomon, T. E., (1986) *Reg. Peptides* 15, pp 205–217) to this conjugate and the mixture used to immunize rabbits. The antigastrin-antiserum titers found were comparable to the antibody titers that had been obtained by use of conventional gastrin conjugates such as gastrin-ribonuclease or gastrin-bovine serum albumin ((8) Geiger, R., Moroder, L., and Wuensch E. (1984), in *Peptides* 1984 (Ragnarsson, U., Ed.), Almquist and Wiksell Int., Stockholm, pp. 451–456).

What is claimed is:

1. A hinge peptide of the general formula

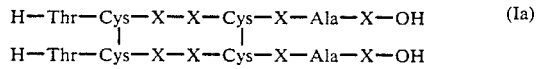
(Ia)

wherein each X is independently the amino acid proline or an amino acid having an equivalent steric hindrance.

2. The hinge peptide of claim 1 wherein each X is proline.

3. The hinge peptide of claim 1 wherein at least some of the amino acid residues are protected by a protecting group.

4. The hinge peptide of claim 2 wherein at least some of the amino acid residues are protected by a protecting group.

5. The hinge peptide of claim 1, wherein at least two of the amino acids are anchor points for building synthetic immunogens.

6. The hinge peptide of claim 2, wherein at least two of the amino acids are anchor points for building synthetic immunogens.

7. The hinge peptide of claim 1 wherein all of the amino acids have an L-configuration.

8. The hinge peptide of claim 2 wherein all of the amino acids have an L-configuration.

* * * * *